(12) United States Patent
Li et al.

(10) Patent No.: US 7,314,956 B2
(45) Date of Patent: Jan. 1, 2008

(54) MULTIFUNCTIONAL CARRIER FOR THE DELIVERY OF A PHARMACOLOGICAL AGENT OR GENETIC MATERIAL INTO A CELL

(75) Inventors: Frank Q. Li, Montgomery Village, MD (US); Yong Liang Chu, Rockville, MD (US); Shuren Zhu, Silver Spring, MD (US); Jian-Tai Qiu, Rockville, MD (US); Wan-Ching Lai, Rockville, MD (US)

(73) Assignee: Vaxim, Inc., Rockville, MD (US)

( * ) Notice: Subject to any disclaimer, the term of this patent is extended or adjusted under 35 U.S.C. 154(b) by 385 days.

(21) Appl. No.: 10/137,355

(22) Filed: May 3, 2002

(65) Prior Publication Data

US 2003/0068379 A1   Apr. 10, 2003

Related U.S. Application Data

(60) Provisional application No. 60/310,492, filed on Aug. 8, 2001.

(51) Int. Cl.
| | |
|---|---|
| C07C 233/02 | (2006.01) |
| C07C 233/04 | (2006.01) |
| C07C 233/05 | (2006.01) |
| C07C 233/07 | (2006.01) |
| C07C 233/17 | (2006.01) |
| C07C 233/31 | (2006.01) |
| A61K 31/16 | (2006.01) |

(52) U.S. Cl. ........................ 564/153; 514/616
(58) Field of Classification Search .................... None
See application file for complete search history.

(56) References Cited

U.S. PATENT DOCUMENTS

| 4,289,872 | A | 9/1981 | Denkewalter et al. |
|---|---|---|---|
| 4,360,646 | A | 11/1982 | Denkewalter et al. |
| 4,410,688 | A | 10/1983 | Denkewalter et al. |
| 4,587,329 | A | 5/1986 | Tomalia et al. |
| 5,229,490 | A | 7/1993 | Tam |
| 5,338,532 | A | 8/1994 | Tomalia et al. |
| 5,527,524 | A | 6/1996 | Tomalia et al. |
| 5,714,166 | A | 2/1998 | Tomalia et al. |
| 5,882,645 | A | 3/1999 | Toth et al. |
| 6,121,236 | A | 9/2000 | Ben-Sasson |
| 6,194,543 | B1 | 2/2001 | Florence et al. |
| 6,245,358 | B1 | 6/2001 | Adami et al. |

OTHER PUBLICATIONS

Yang, et al., "Controlled Release Tacrine Delivery System for the Treatment of Alzheimer's Disease", Drug Delivery,8, 93-98 (2001).
Chandy, et al., "Development of Poly(Lactic Acid)/Chitosan Co-Matrix Microspheres: Controlled Release of Taxol-Heparin for Preventing Restenosis", Drug Delivery, 8, 77-86 (2001).
Pignatello, et al., "Preparation and Analgesic Activity of Eudragit RS100® Microparticles Containing Diflunisal", Drug Delivery, 8, 35-45 (2001).
Singh, et al., "Receptor-Mediated Gene Delivery to HepG2 Cells by Ternary Assemblies Containing Cationic Lipsomes and Cationized Asialoorosomucoid", Drug Delivery, 8, 29-34 (2001).
Petrikovics, et al., "In Vitro Studies on Sterically Stabilized Liposomes (SL) As Enzyme Carriers in Organophosphorus (OP) Antagonism", Drug Delivery, 7, 83-89 (2000).
Gupta, et al., "Biodegradable Polymer Microspheres as Vaccine Adjuvants and Delivery Systems", Brown, et al., (eds), Dev. Biol. Stand, Basel, Karger,92, 63-78 (1998).
Zou, et al., "Effectiveness of Water Soluble Poly(L-Glutamic Acid)-Camptothecin Conjugate Against Resistant Human Lung Cancer Xenografted in Nude Mice", International Journal of Oncology, 18, 331-336 (2001).
Oldham, et al., "Comparison of Action of Paclitaxel and Poly(L-Glutamic Acid)-Paclitaxel Conjugate in Human Breast Cancer Cells", International Journal of Oncology, 16, 125-132 (2000).
Pechar, et al., "Poly(Ethylene Glycol) Multiblock Copolymer as a Carrier of Anti-Cancer Drug Doxorubicin", Bioconjug Chem., 11, 2, 131-139 (2000).
Kratz, et al., "Drug-Polymer Conjugates Containing Acid-Cleavable Bonds", Critical Reviews™ in Therapeutic Drug Carrier Systems, 16, 3, 245-288 (1999).
Sezaki, et al., "Macromolecule-Drug Conjugates in Targeted Cancer Chemotherapy", CRC Critical Reviews in Therapeutic Drug Carrier Systems, 1, 1, 1-38 (1984).
Kovacs, et al., "Comparison of Mechanisms of Action of Leuteinizing Hormone-Releasing Hormone (LHRH) Antagonist Cetrorelix and LHRH Agonist Triptorelin on the Gene Expression of Pituitary LHRH Receptors in Rats", PNAS, vol. 98, No. 21, 12197-12202 (2001).
Tedder, et al., "Amino-Acids and Proteins", Basic Organic Chemistry, Chapter 6, 305-342, London, John Wiley & Sons (1972).
Picone, et al., "Peptide T. Revisited: Conformational Mimicry of Epitopes of Anti-HIV Proteins", Journal of Peptide Science, 7, 197-207 (2001).

*Primary Examiner*—Brian Davis

(57) ABSTRACT

The present invention provides a drug delivery vehicle that can improve the pharmacokinetics of pharmacological agents. The invention relates to a multifunctional carrier capable of delivering a carried material such as a pharmacological agent or genetic material to a recipient. The multifunctional carrier includes a multifunctional core and a plurality of adduct molecules bonded thereto. The molecular carrier has surface functional groups which can be associated with a carried material. The carried material can be associated with the molecular carrier through covalent interactions or ionic interactions. The polyvalent core can be ethylene-diamine tetraacetic acid (EDTA) or succinic acid. The invention also relates to methods for producing and using such molecules.

2 Claims, 15 Drawing Sheets

MULTIFUNCTIONAL CARRIER FOR THE DELIVERY OF A PHARMACOLOGICAL AGENT OR GENETIC MATERIAL INTO A CELL

CROSS-REFERENCE TO RELATED APPLICATIONS

This application claims the benefit of U.S. Provisional Application No. 60/310,492, which was filed on Aug. 8, 2001.

BACKGROUND OF THE INVENTION

1. Field of the Invention

The invention relates generally to intracellular transports and transport complexes and, in particular, to polyfunctional molecules capable of delivering a desired pharmacological agent to a recipient. The invention also relates to methods for producing and using such molecules.

2. Background of the Technology

Many valuable compounds must be discarded as potential pharmaceuticals because of their pharmacokinetic profile. In some cases, the compound is cleared from circulation too rapidly, or accumulates to undesired levels in the kidneys or other organs, or is labile to digestive or circulatory enzymes or factors.

In light of the importance of surmounting the undesired pharmacokinetics of many compounds, a variety of drug delivery systems, such as liposomes, microspheres, antibodies, etc., all aimed at improving the therapeutic index and specificity of potential pharmaceuticals have been suggested (U.S. Pat. No. 6,245,358 (Adami, et al.).

For example, various efforts to encapsulate or entrap the desired pharmaceutical have been described (e.g., Yang, et al., "Controlled Release Tacrine Delivery System For The Treatment Of Alzheimer's Disease", Drug Deliv., 8, 2, 93-98 (2001); Chandy, et al., "Development Of Poly (Lactic Acid)/Chitosan Co-Matrix Microspheres: Controlled Release Of Taxol-Heparin For Preventing Restenosis", Drug Deliv., 8, 2, 77-86 (2001); Pignatello, et al., "Preparation And Analgesic Activity Of Eudragit RS100 Microparticles Containing Diflunisal", Drug Deliv., 8, 1, 35-45 (2001). Likewise, liposome drug delivery formulations have been described (Singh, et al., "Receptor-Mediated Gene Delivery To Hepg2 Cells By Ternary Assemblies Containing Cationic Liposomes And Cationized Asialoorosomucoid", Drug Deliv., 8, 1, 29-34 (2001); Petrikovics, et al., "In Vitro Studies On Sterically Stabilized Liposomes (SL) As Enzyme Carriers In Organophosphorus (OP) Antagonism", Drug Deliv., 7, 2, 83-89 (2001). Such approaches to drug delivery are reviewed by Gupta, et al. ("Biodegradable Polymer Microspheres As Vaccine Adjuvants And Delivery Systems", Dev Biol Stand, 92, 63-78 (1998).

Additionally, active agents have been coupled or conjugated to polymeric compounds in an attempt to improve the delivery of the active agent. For example, camptothecin has been conjugated to poly(L-glutamic acid) (PG) (Zou, et al., "Effectiveness Of Water Soluble Poly(L-Glutamic Acid)-Camptothecin Conjugate Against Resistant Human Lung Cancer Xenografted In Nude Mice", Int J Oncol., 18, 2, 331-336 (2001). The anticancer agent, paclitaxel, has likewise been conjugated to poly(L-glutamic acid) and found to possess improved pharmacokinetic properties (Oldham, et al., "Comparison Of Action Of Paclitaxel And Poly(L-Glutamic Acid)-Paclitaxel Conjugate In Human Breast Cancer Cells", Int J Oncol., 16, 1, 125-32 (2000). Similarly, Pechar, et al. describe the synthesis of a water-soluble polymer drug carrier system based on biodegradable poly (ethylene glycol) block copolymer, and its use to produce a conjugate of doxorubicin. The copolymer consisted of PEG blocks of molecular weight 2000 linked by means of an oligopeptide having amino end groups. Each of the oligopeptide blocks incorporated in the carrier contained three carboxylic groups of which some were used for attachment of the doxorubicin via an enzymatically cleavable tetrapeptide spacer Gly-Phe-Leu-Gly (Pechar, et al., "Poly(Ethylene Glycol) Multiblock Copolymer As A Carrier Of Anti-Cancer Drug Doxorubicin", Bioconjug Chem., 11, 2, 131-139 (2000). Drug polymer conjugates containing acid-cleavable bonds are reviewed by Kratz, et al., "Drug Polymer Conjugates Containing Acid-Cleavable Bonds", Crit Rev Ther Drug Carrier Syst., 16, 3, 245-88 (1999). Such approaches to drug delivery are reviewed by Sezaki, et al. ("Macromolecule-Drug Conjugates In Targeted Cancer Chemotherapy", Crit Rev Ther Drug Carrier Syst., 1, 1, 1-38 (1984).

Drug delivery systems comprising dendrimers and dendrimer conjugates are also known. See, for example, U.S. Pat. Nos. 4,289,872; 4,360,646; 4,410,688, 4,587,329; 5,229,490; 5,338,532; 5,527,524; 5,714,166; 5,882,645; and 6,194,543.

Despite such efforts, a need continues for a delivery vehicle that can improve the pharmacokinetics of pharmacological agents. The present invention is directed to such a need.

SUMMARY OF THE INVENTION

According to a first aspect of the invention, a molecular carrier comprising a central multivalent core and a plurality of adduct molecules bonded thereto is provided wherein the molecular carrier is represented by the formula:

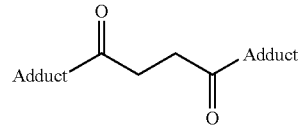

wherein "Adduct" represents adduct moieties which can be the same or different from one another and wherein the adduct moieties comprise the residue of an amino acid. According to a second aspect of the invention, the molecular carrier is represented by the formula:

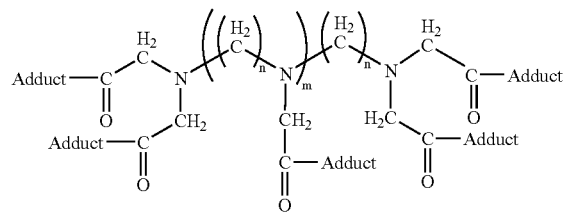

or the formula:

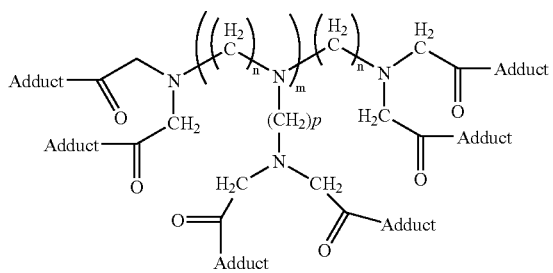

wherein n is an integer of 2 or greater, m is 0 or a positive integer and p is a positive integer and wherein "Adduct" represents adduct moieties which can be the same or different from one another and wherein the adduct moieties comprise the residue of an amino acid.

According to a further aspect of the invention, one or more of the adduct moieties comprise a moiety represented by the formula:

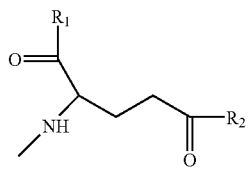

or the formula:

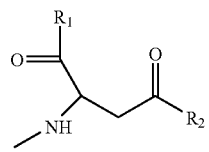

wherein each $R_1$ and each $R_2$ independently represent a hydroxyl group, a residue of an amino acid, or a polyfunctional amine. According to a further aspect of the invention, one or more of the adduct moieties comprise a moiety represented by the formula:

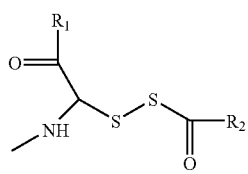

wherein each $R_1$ and each $R_2$ independently represent a hydroxyl group, a residue of an amino acid, or a polyfunctional amine.

A pharmacological agent/molecular carrier complex is also provided. The pharmacological agent/molecular carrier complex includes a molecular carrier as set forth above and a pharmacological agent wherein the pharmacological agent is associated with one of the adduct moieties. The pharmacological agent can be a non-peptide drug, a protein, a peptide, a steroid or a hormone. For example, the pharmacological agent can be a peptide antigen capable of eliciting an immune response, an opiate peptide an LHRH antagonist, a non-peptide drug such as paclitaxel, or an angiogenic agent which can inhibit or stimulate angiogenesis.

The molecular carrier can include one or more maleimide groups and the pharmacological agent can be covalently associated with the molecular carrier by reaction of a thiol group on the pharmacological agent with the maleimide group on the molecular carrier. The pharmacological agent/molecular carrier complex can be dispersed in a solution as an emulsion or suspension or immobilized to a solid support.

A genetic material/molecular carrier complex comprising a molecular carrier as set forth above and genetic material, wherein the genetic material is associated with one of the adduct moieties, is also provided. The molecular carrier can have one or more positively charged surface functional groups and the genetic material can be ionically accociated with the molecular carrier through the one or more positively charged surface functional groups. For example, the molecular carrier can include the residue of a polyfunctional amine and one or more amine groups of the polyfunctional amine can be protonated to form the positively charged surface functional groups.

A method of forming a molecular carrier is also provided. The method includes covalently bonding a plurality of adduct molecules to a central multivalent core molecule by reacting a nucleophilic group on each adduct molecule with an electrophilic group on the multivalent core molecule. The multivalent core molecule comprises at least two electrophilic groups. According to a further embodiment of the invention, the multivalent core molecule is a polyfunctional-carboxylic acid.

According to a further aspect of the invention, a molecular carrier comprising a central multivalent core and a plurality of adduct molecules bonded thereto is provided wherein the central multivalent core is the residue formed by the nucleophilic acyl substitution reaction of each of the amino groups of a polyfunctional-amine with a carboxylic acid group of an adduct molecule. According to this aspect of the invention, the polyfunctional-amine can be: a benzene-tetramine; tri (carboxymethyl)amine; ((Lys)$_2$Lys)$_3$-(TFA), wherein TFA is a tri-functional amine such as tris(2-aminoethyl)amine; diethylaminetriamine; triethylenetetramine; or NH$_2$((CH$_2$)$_n$ NH)$_m$(CH$_2$)$_n$NH$_2$, wherein n and m are integers that may be the same or different and which may vary throughout the molecule.

DETAILED DESCRIPTION OF THE INVENTION

Figure 1A:
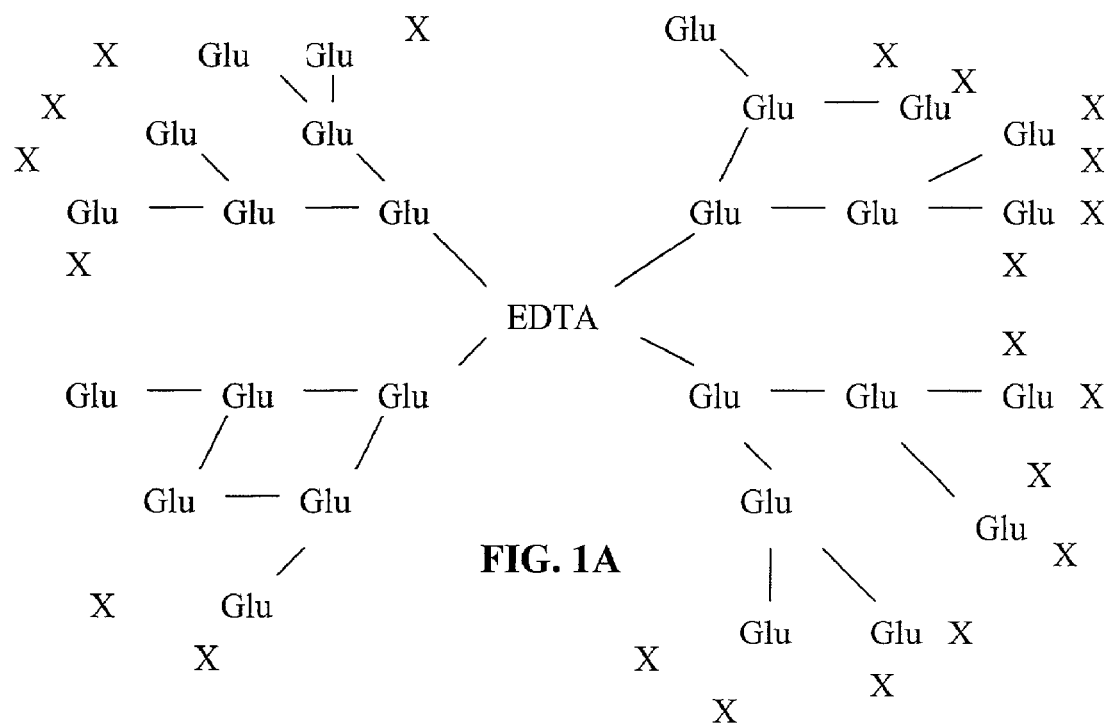
FIGS. 1A and 1B depict schematic structures for preferred conjugates of the present invention.

The present invention provides a drug delivery vehicle that can improve the pharmacokinetics of pharmacological agent. The invention relates to multifunctional molecules capable of delivering pharmacological agents to a recipient. The invention also relates to methods for producing and using such molecules.

In detail, the invention provides a drug delivery system comprising a molecular carrier, the carrier comprising a central polyvalent core, the core having a plurality of adduct molecules bound thereto, wherein each of the bound adduct molecules possesses multiple reactive groups for binding a desired pharmacological agent.

The invention further provides the embodiment of such drug delivery system wherein the core molecule will array the bound adduct molecules in a symmetrical manner.

The invention further provides the embodiment of such drug delivery system wherein the polyvalent core is bivalent, trivalent, tetravalent, pentavalent or hexavalent. The invention further provides the embodiment of such drug delivery system wherein the polyvalent core is bivalent, especially wherein the bivalent core is ethylenediamine. The invention further provides the embodiment of such drug delivery system wherein the polyvalent core is trivalent especially wherein the trivalent core is tris (2-aminoethylamine), 1,2,3-propanetricarboxylic acid, 2-hydroxy propane-1,2,3-tricarboxylate, 1-hydroxy propane-1,2,3-tricarboxylate, tri(carboxymethyl)amine, diethylaminetriamine, ((Lys)$_2$Lys)$_3$-(TFA), ((Orni)$_2$ Orni)$_3$-(TFA), ((DAB)$_2$ DAB)$_3$- (TFA), or any combination of DAB (diaminobutyric acid), Orni (ornithene) or Lys (lysine) adducts covalently linked to a tri-functional amine (TFA) such as tris (2-aminoethyl)amine. The invention further provides the embodiment of such drug delivery system wherein the polyvalent core is tetravalent, especially wherein the tetravalent core is benzenetetracarboxylic acid, a benzenetetramine, a cyclopentanetetracarboxylic acid, a butanetetracarboxylic acid, an ethylenediamine tetraalkylcarboxylic acid, an ethylene glycol-bis(beta-aminoethyl ether)-N,N,N',N' tetraacetic acid, a 1,2-Diaminocyclohexane-N,N,N',N' tetraacetic acid, ((COOH)CH$_2$)$_2$N(CH$_2$)$_3$NCH$_2$COOH(CH$_2$)$_3$NH$_2$, (COOH) CH$_2$N(CH$_2$)$_3$NCH$_2$COOH(CH$_2$)$_2$NH$_2$, or triethylenetetramine. The invention further provides the embodiment of such drug delivery system wherein the tetravalent core is ethylenediamine tetraacetate. The invention further provides the embodiment of such drug delivery system wherein the polyvalent core is pentavalent, especially wherein the pentavalent core is diethylenetriamine-pentaacetic acid. The invention further provides the embodiment of such drug delivery system wherein the polyvalent core is hexavalent, especially wherein the hexavalent core is a triethylenetetraminehexaacetic acid. The invention further provides the embodiment of such drug delivery system wherein the polyvalent core is NH$_2$((CH$_2$)$_n$NH)$_m$(CH$_2$)$_n$NH$_2$, where n and m are integers that may be the same or different, and which may vary throughout the molecule.

The invention further provides the embodiment of such drug delivery system wherein the reactive groups of the adduct molecules are selected from the group consisting of amino groups and carboxylic acid groups. The invention further provides the embodiment of such drug delivery system wherein the adduct molecules are bivalent. The invention further provides the embodiment of such drug delivery system wherein the amino or carboxylic acid groups are the amino or carboxylic acid groups of an amino acid. The invention further provides the embodiment of such drug delivery system wherein the amino acid is glutamic acid, aspartic acid, lysine or arginine.

The invention further provides the embodiment of such drug delivery system wherein at least some of the adduct molecules are bound to other adduct molecules. The invention further provides the embodiment of such drug delivery system wherein at least some of the adduct molecules are associated with a pharmacological agent. The invention further provides the embodiment of such drug delivery system wherein at least some of the adduct molecules are associated with one pharmacological agent, and at least some of the adduct molecules are associated with a different pharmacological agent. The invention further provides the embodiment of such drug delivery system wherein the pharmacological agent is selected from the group consisting of small organic molecules, proteins, peptides, steroids and hormones.

According to a preferred embodiment of the invention, the pharmacological agent is a peptide antigen which is capable of eliciting an immune response. It is known that synthetic peptides can induce antibodies reactive with their cognate sequences in the native proteins (i.e., that synthetic peptide and native protein comprise the same epitope). Specific antibodies are useful as reagents in various investigations. Furthermore, peptide antigens made by known peptide synthesis techniques are useful for producing immunogens and for immunoprophylaxis and in affinity purification of proteins, antibodies, or other molecules. Peptide antigens are disclosed in U.S. Pat. No. 5,882,645, which is hereby incorporated by reference in its entirety.

According to a further embodiment, a plurality of peptide antigens are conjugated to a molecular carrier according to the invention. The peptide antigens can be covalently conjugated to the molecular carrier via reactive groups (e.g., amine or carboxylic acid groups) on the peptide. For example, an amino group on the peptide can be reacted with a carboxylic acid group on the molecular carrier or vice versa.

According to a further embodiment of the invention, the pharmacological agent is a pain killer such as an opiate peptide. Opiate peptides can also be covalently conjugated to the molecular carrier via reactive groups (e.g., amine or carboxylic acid groups) on the peptide.

According to a further embodiment of the invention, the pharmacological agent is a contraceptive such as an LHRH antagonist. Various LHRH antagonists are known. For example, the LHRH antagonist cetrorelix is disclosed in Kovacs et al., "Comparison of Mechanisms of Action of Leuteinizing Hormone-releasing Hormone (LHRH) Antagonist Cetrorelix and LHRH Agonist Triptorelin on the Gene Expression of Pituitary LHRH Receptors in Rats", PNAS, Vol. 98, No. 21 (2001).

According to a further embodiment of the invention, the pharmacological agent can be an angiogenic agent capable of modulating the development of blood vessels in mammals. Angiogenic agents are disclosed in U.S. Pat. No. 6,121,236, which is hereby incorporated by reference in its entirety.

Other pharmacological agents which can be conjugated to molecular carriers according to the invention include non-peptide drugs such as paclitaxel. Paclitaxel, which is a known anti-cancer agent, can be conjugated to the molecular carrier using known techniques. Conjugates of paclitaxel and glutamic acid are, for example, disclosed by Oldham, et al. in Int. J. Oncol., 16, 1, 125-32 (2000).

Additionally, a genetic material can be conjugated to the molecular carrier according to the invention. The transfer of genetic material into cells has many potential uses as therapeutic and/or diagnostic agents for human illness. Genetic material can be transfected and subsequently transcribed and expressed to make new proteins within cells, replacing either aberrant proteins or absent proteins caused by genetic errors. In addition, smaller pieces of genetic material including either DNA or RNA, can be transfected into cells to alter cell function or edit specific messenger RNA's to correct other types of genetic defects. Further, synthetic genetic material, such as modified forms of antisense oligonucleotides, can be transferred into cells to block the production of specific proteins. This may be useful in suppressing cells that grow abnormally, such as cancer cells, or in the alteration of normal cell functions, such as immunosuppression for organ transplantation. Small pieces of genetic material, such as aptimers, can also function as drugs, and the transfer of these forms of nucleic acids can specifically alter cellular functions in a manner similar to a pharmaceutical.

The molecular carriers of the present invention may be complexed with genetic material and used for gene therapy in mammals including humans. A method for preventing or treating a disease may comprise transfecting a mammalian cell with a molecular carrier according to the invention complexed with genetic material. As discussed earlier, genetic material may be transfected into cells for a variety of reasons including the production of proteins within cells, altering cell function, correcting genetic defects, and the like. In this manner, genetic diseases or conditions may be prevented or treated using the complex of a molecular carrier and genetic material according to the present invention.

When the carried material is genetic material, the surface of the dendrimer preferably comprises of a predominance of positively charged surface functional groups. The positive functionality can achieved by providing amino surface functional groups on the molecular carrier. When the surface functional groups of the molecular carrier are carboxylic acid groups, the positively charged functional groups can be introduced chemically. For example, polyfunctional amines such as ethylene diamine, spermine or spermidine can be reacted with the carboxylic acid surface functional groups on the molecular carrier. Additionally, compounds comprising both a nucleophilic group (e.g. an amine) and one or more positively charged groups (e.g., quaternary onium salts) can be reacted with the electrophilic carboxylic acid groups to provide the positively charged surface groups. The above materials are only exemplary and other compounds and techniques can be used according to the invention to provide positively charged surface functional groups on the molecular carrier.

As set forth above, the carried material can be associated covalently or ionically with the multi-functional carrier. When the carried material is a peptide having a cysteine residue, the peptide can be associated with maleimide functional groups on the molecular carrier. These maleimide groups can be provided by reacting surface functional amino groups on the carrier with compounds containing both maleimide groups and electrophilic groups (e.g., carboxylic acid groups). Examples of such compounds include 3-maleimidopropionic acid and 4-(N-maleimidomethyl)cyclohexane-1-carboxylate. If the multifunctional carrier comprises nucleophilic (e.g., carboxylic acid) surface functional groups, the amino groups can be provided by reacting the carboxylic acid surface functional groups with a polyfunctional amine such as spermine, spermidine or ethylenediamine.

The present invention further provides a drug delivery system wherein the molecular carrier is soluble or solubilized. The invention further provides the embodiment of such drug delivery system wherein the molecular carrier is immobilized to a solid support.

The invention further provides a method for improving the pharmacokinetic profile of a pharmacological agent which comprises forming a delivery system comprising a molecular carrier, the carrier comprising a central polyvalent core, the core having a plurality of adduct molecules bound thereto, wherein the wherein adduct molecules have reactive groups, and the pharmacological agent is bound to the reactive groups of the adduct molecules.

The present invention relates to a drug delivery system comprising a molecular carrier, which is composed of a central polyvalent core having a plurality of adduct molecules bound thereto, wherein each of the bound adduct molecules possesses multiple reactive groups for binding a desired pharmacological agent.

The reactive groups of the adduct molecules are selected so that at least one reactive group will be capable of binding (e.g., ionically or covalently) to a group of a desired pharmacological agent. The presence of the adduct molecules thus permits multiple molecules of the pharmacological agent to become associated to a single core.

As used herein, the term pharmacological agent is intended to be broadly construed, and to encompass small organic molecules (e.g., inhibitors, opiates, anti-inflammatory agents), as well as proteins (e.g., enzymes, clotting factors such as tissue plasminogen activator, etc.), peptides (e.g., protein mimetics, inhibitors, vaccines, etc.), steroids, hormones (e.g., insulin, progesterone, estrogen, etc.), nucleic acid molecules (DNA, and RNA), etc.

The term "conjugate molecules" as used herein is intended to refer to a core molecule associated with at least one, and preferably, two or more adduct molecules. The core molecule will be polyvalent, thus having the ability to become associated with two or more, and preferably four or more adduct molecules. In a preferred embodiment, the core molecule will array such adduct molecules in a symmetrical manner so as to minimize any steric interference, and maximize the solubility of the pharmacological agent-adduct-core complex. Examples of suitable core molecules include bivalent, trivalent, tetravalent, pentavalent, hexavalent, etc. molecules including:
  Bivalent Molecules:
    ethylenediamine;
    succinic acid;

diaminopropane; and
diaminobutane;
Trivalent Molecules:
Tris(2-aminoethyl)amine;
Tris(3-aminopropyl)amine;
Bis(3-aminopropyl)amine;
Spermidine;
Diethylenetriaminepentaacetic acid;
1,2,3-Propanetricarboxylic acid;
2-hydroxy-1-Hydroxypropane-1,2,3-tricarboxylate
Tri(carboxymethyl)amine;
Diethylaminetriamine;
Tetravalent Molecules:
Benzenetetracarboxylic acids, including:
    1,2,4,5 benzenetetracarboxylic acid
    1,2,3,5 benzenetetracarboxylic acid
    1,2,3,4 benzenetetracarboxylic acid
Benzenetetramines, including,
    1,2,4,5 benzenetetramine
Cyclopentanetetracarboxylic acid, including:
    cis, cis, cis, cis, 1,2,3,4 cyclopentanetetracarboxylic acid
Butanetetracarboxylic acids, including:
    1,2,3,4 butanetetracarboxylic acid
Ethylenediamine tetraalkylcarboxylic acids, including:
    ethylenediamine tetraacetate
Ethylene glycol-bis(beta-aminoethylether)-N,N,N',N' tetraacetic acid
1,2-Diaminocyclohexane-N,N,N',N' tetraacetic acid, including:
    trans-1,2-Diaminocyclohexane-N,N,N',N' tetraacetic acid
$((COOH)CH_2)_2N(CH_2)_3NCH_2COOH(CH_2)_3NH_2$
$(COOH)CH_2N(CH_2)_3NCH_2COOH(CH_2)_2NH_2$
Triethylenetetramine; and
Spermine;
Pentavalent Molecules:
Diethylenetriaminepentaacetic acid; and
Spermidinepentaacetic acid;
Hexavalent Molecules:
Triethylenetetraminehexaacetic acid; and
Sperminehexaacetic acid;
$((Lys)_2Lys)_3$-(TFA);
$[(Ornithene)_2Ornithene]_3$-(TFA); and
$[(Diamino\ butyric\ acid)_2\ Diamino\ butyric\ acid]_3$-(TFA).

"TFA" in the above formulae represents a tri-functional amine such as tris(2-aminoethyl)amine. Other polyvalent molecules that may be employed comprise $NH_2((CH_2)_n NH)_m (CH_2)_n NH_2$, where n and m are integers that may be the same or different, and which may vary throughout the molecule. Ethylenediamine tetraacetate (EDTA), succinic acid and $((Lys)_2Lys)_3$-(TFA) are preferred core molecules.

Figure 1B:
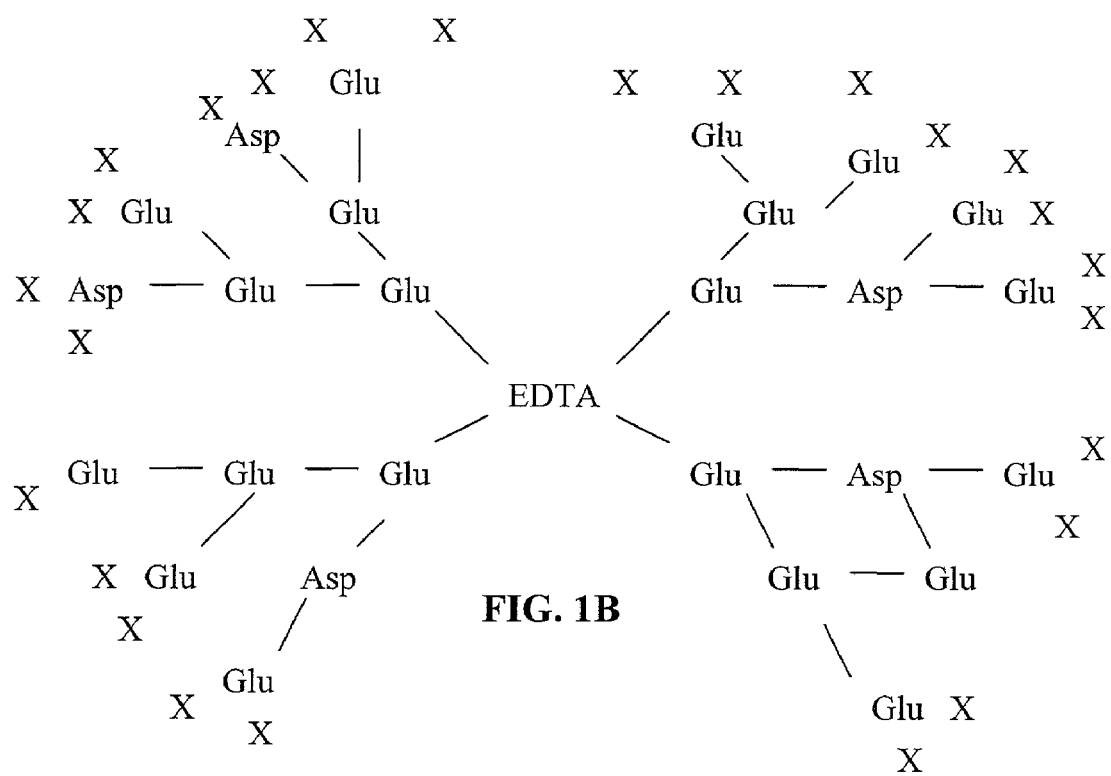
Figure 2A:
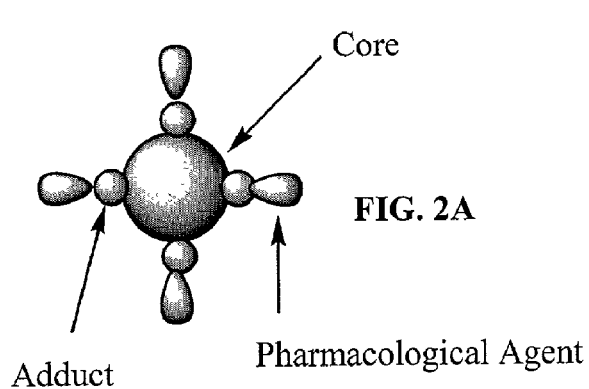
FIGS. 2A through 2E illustrate preferred conjugates of the present invention wherein the core molecule of the multifunctional carrier is denoted by a large circle, the adduct molecules are shown as smaller circles and the carried material (i.e., the pharmacological agent) is shown as an ellipsoid.
Figure 2B:
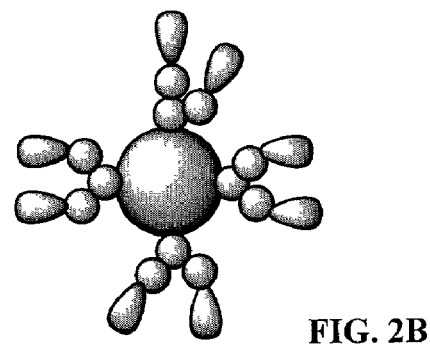
Figure 2C:
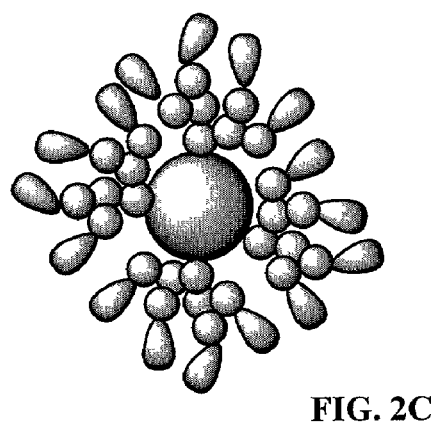
Figure 2D:
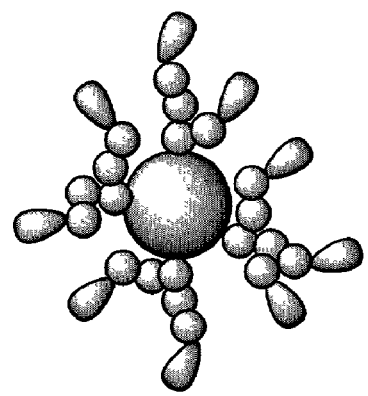
Figure 2E:
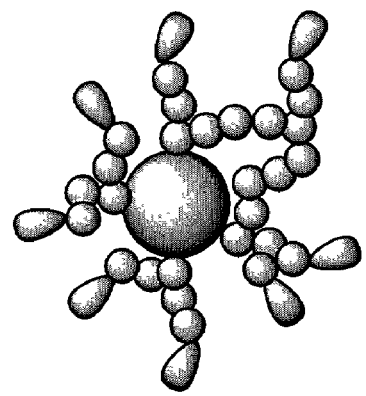

The adduct molecules that may be used in accordance with the present invention will possess reactive groups, such as amino groups, carboxylic acid groups, etc. Preferably, the adduct molecules will be multivalent, and as such have at least one group capable of associating with the core and a second group that is capable of associating with an adduct molecule or with a pharmacological agent. In a preferred embodiment, the reactive groups will be carboxylic acid groups. In a preferred embodiment, the adduct will be glutamic acid (Glu) or aspartic acid (Asp), although other amino acids such as lysine (Lys) or arginine (Arg) may be employed. FIGS. 1A and 1B show molecular carriers comprising an EDTA core and glutamic acid adducts (FIG. 1A) and an EDTA core and glutamic and aspartic acid adducts (FIG. 1B).

Thus, the adducts conjugated to the core may be the same amino acid as shown in FIG. 1A or, alternatively, mixtures of different amino acids may be employed as shown in FIG. 1B. In a further embodiment, such carboxylic acid adducts can themselves be adducted by additional amino acids, so as to produce peptide or pseudo-peptide carboxylic acid adducts, which each may be homogeneous or heterogeneous in composition, length and/or branching. In a preferred embodiment, the core will comprise multiple adduct "strands" which may be branched or unbranched, and which may be connected or not connected to other strands attached to the same core.

According to a pereferred embodiment of the invention, the molecular carrier is represented by the formula:

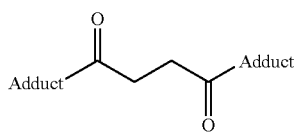

wherein "Adduct" represents adduct moieties which can be the same or different from one another and wherein the adduct moieties comprise the residue of an amino acid.

According to a further preferred embodiment of the invention, the molecular carrier is represented by the formula:

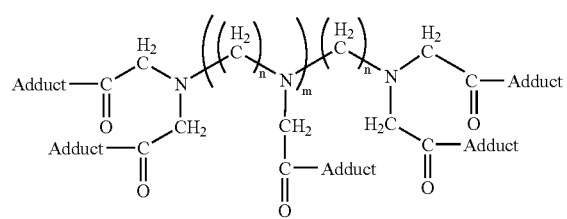

or by the formula:

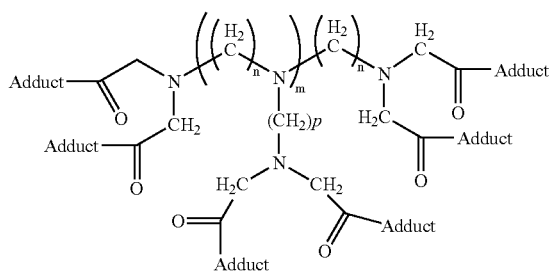

wherein n is an integer of 2 or greater, m is 0 or a positive integer and p is a positive integer and wherein "Adduct" represents adduct moieties which can be the same or different from one another and wherein the adduct moieties comprise the residue of an amino acid.

FIGS. 2A through 2E depict schematic structures of exemplary conjugates of the present invention illustrating this aspect of the invention. As is apparent from the figures, all of the adduct molecules need not be associated with a pharmacological agent.

Any of a variety of reagents and methods can be used to bind the adduct molecules to the reactive groups of the core molecule. Most preferably, however, 1-ethyl-3-(3-dimethylaminopropyl)-carbodiimide (EDC) is employed for this purpose. EDC is a water-soluble derivative of carbodiimide. Carbodiimide catalyzes the formation of amide bonds between carboxylic acids or phosphates and amines by activating carboxyl or phosphate to form an O-urea derivative. This derivative reacts readily with nucleophiles. The reagent can be used to make ether links from alcohol groups and ester links from acid and alcohols or phenols, and peptide bonds from acid and amines (Tedder, et al., "Amino-Acids and Proteins", In: Basic Organic Chemistry, Chapter 6, pp. 305-342, London, John Wiley & Sons (1972)). Carbodiimide is often used in the synthesis of peptides as the water-soluble derivative EDC or as the organic soluble derivative, N,N'-dicyclohexyl-carbodiimide (DCC).

Additionally, the conjugates of the present invention may be used to conjugate a single pharmacological agent, or two or more different pharmacological agents. One aspect of the present invention concerns a means for concentrating the delivery of a pharmacological agent to a site of need. In this regard, the conjugates of the present invention may have a pharmacological agent associated with one or more of its adduct molecules and a receptor, receptor ligand, etc. associated with another of such adduct molecules.

Figure 3A:
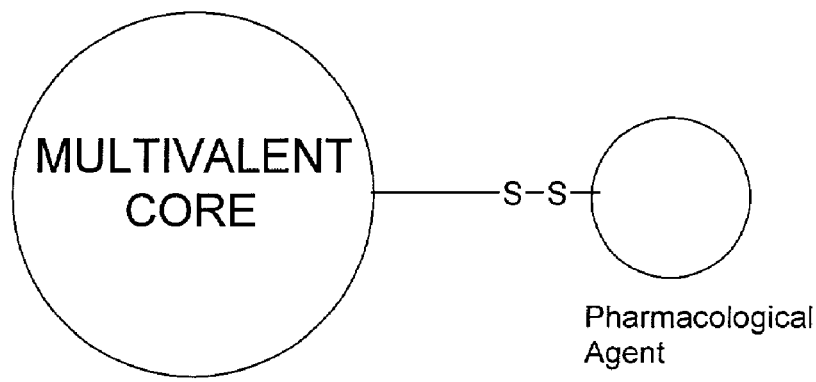
FIG. 3 schematically illustrates conjugates having cleavable adducts.
Figure 3B:
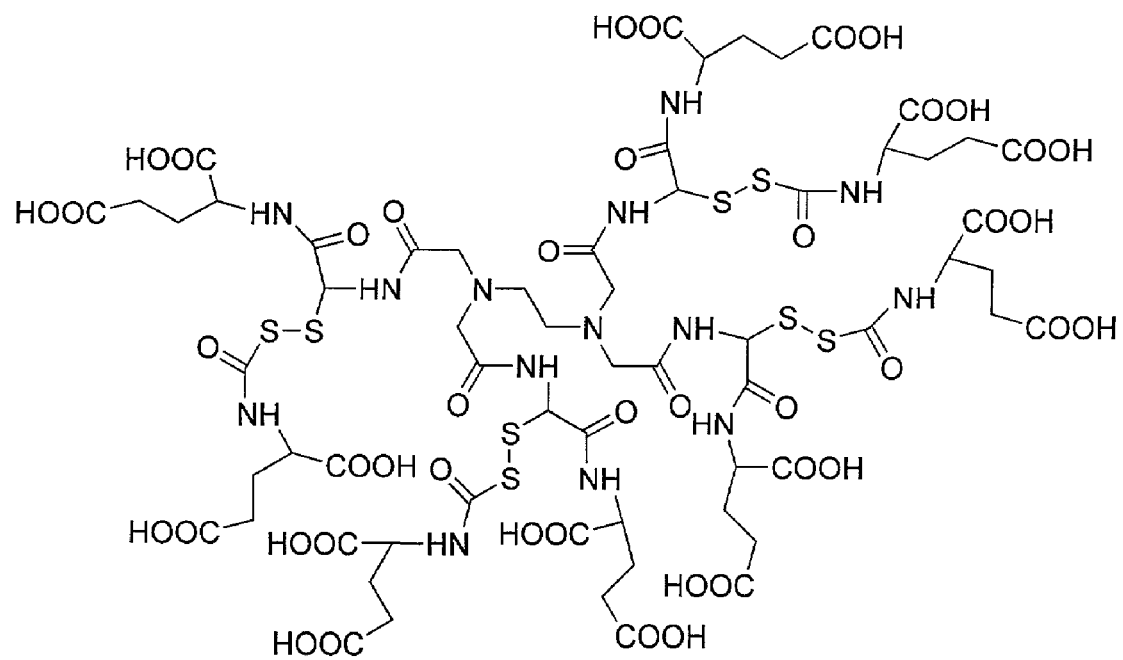

In one embodiment of the present invention, the associated pharmacological agents of the conjugates of the present invention are released from the adducts by enzymes, and/or other factors present within the tissues and organs of recipients, or by solubility or decomposition. Thus, the conjugates of the present invention may be used to effect the sustained release of the associated pharmacological agent, and thereby improve the pharmacokinetic profile of such agent. Preferably, such decomposition will be accomplished through the use of adduct molecules that are labile to enzymes (for example, possessing a cleavable disulfide bond as shown in FIGS. 3A and 3B. By using adduct molecules that are labile to intracellular enzymes, the conjugates of the present invention can be caused to decompose within cells. By using adduct molecules that are labile to digestive enzymes, the conjugates of the present invention can be caused to decompose within the digestive tract, or within or near organs of the digestive system (e.g., stomach, colon, small intestine, gall bladder, etc.). By using adduct molecules that are labile to serum enzymes, the conjugates of the present invention can be caused to decompose within the circulatory system.

In an alternative embodiment, of the present invention, the associated pharmacological agents of the conjugates of the present invention are not designed to be released from the conjugate. Thus, the conjugates of the present invention may be used to effect the localization or concentrating of the associated pharmacological agent at desired sites within the recipient, and thereby improve the pharmacokinetic performance of such agent. For example, the conjugate may be used with peptide or nucleic acid pharmacological agents to provide improved vaccination. A conjugate designed to attack cancer cells may, for example, comprise a tumor specific receptor binding protein and a pharmacological agent (such as an antitumor drug).

In one embodiment, the conjugates of the present invention will be soluble or solubilized (i.e., formulated to be in an emulsion, suspension etc.). Such formulations will be capable of administering the conjugates to recipient patients buy oral, nasal, or inhalation routes, or intramuscularly, subcutaneously, transdermally, intravenously, intraurally or intraocularly. The conjugates of the present invention may similarly be used to provide pharmacological agents to cattle, pigs, sheep, dogs, cats, and other animals.

In an alternative embodiment, conjugates of the present invention containing pharmacological agents may be immobilized onto solid supports (e.g., bandages, sutures, implants, laboratory and food service surfaces, etc.) so as to permit the sustained delivery of the pharmacological agent.

Having now generally described the invention, the same will be more readily understood through reference to the following examples, which are provided by way of illustration, and are not intended to be limiting of the present invention, unless specified.

EXAMPLE 1

Synthesis of EDTA-Glutamic Acid Adducts

The principles of the present invention are illustrated with respect to the synthesis of a preferred tetravalent conjugate molecule, which is formed through the coupling of EDC to EDTA.

EDTA Coupling (First Shell)

(I) Ester synthesis:

To a 50 ml round-bottomed flask, 100 mg of EDTA tetrasodium salt and water (10 ml) was added. Glutamic acid diethyl ester (GDE) hydrochloride (264 mg) and 1-ether-3-(3-dimethylaminopropyl)carbodiimide (EDC) hydrochloride (211 mg) were then added. A clear solution was formed. This solution was stirred at ambient temperature. Thirty minutes later, the solution became cloudy. At this point tetrahydrofuran (THF) (10 ml) was added, and the solution turned clear again. Stirring was continued for 5 hours. The reaction mixture was then partitioned between ethyl acetate (20 ml) and water (20 ml). The separated organic layer was washed with brine (15 ml), dried over anhydrous sodium sulfate (5 g), and evaporated in a rotary evaporator under reduced pressure to give an oil, which was purified over silica gel flash chromatography (1:9 methanol/ethyl acetate) to give the coupling product [EDTA(Glu)$_4$] as a viscous oil (Yield: 92%).

Figure 4:
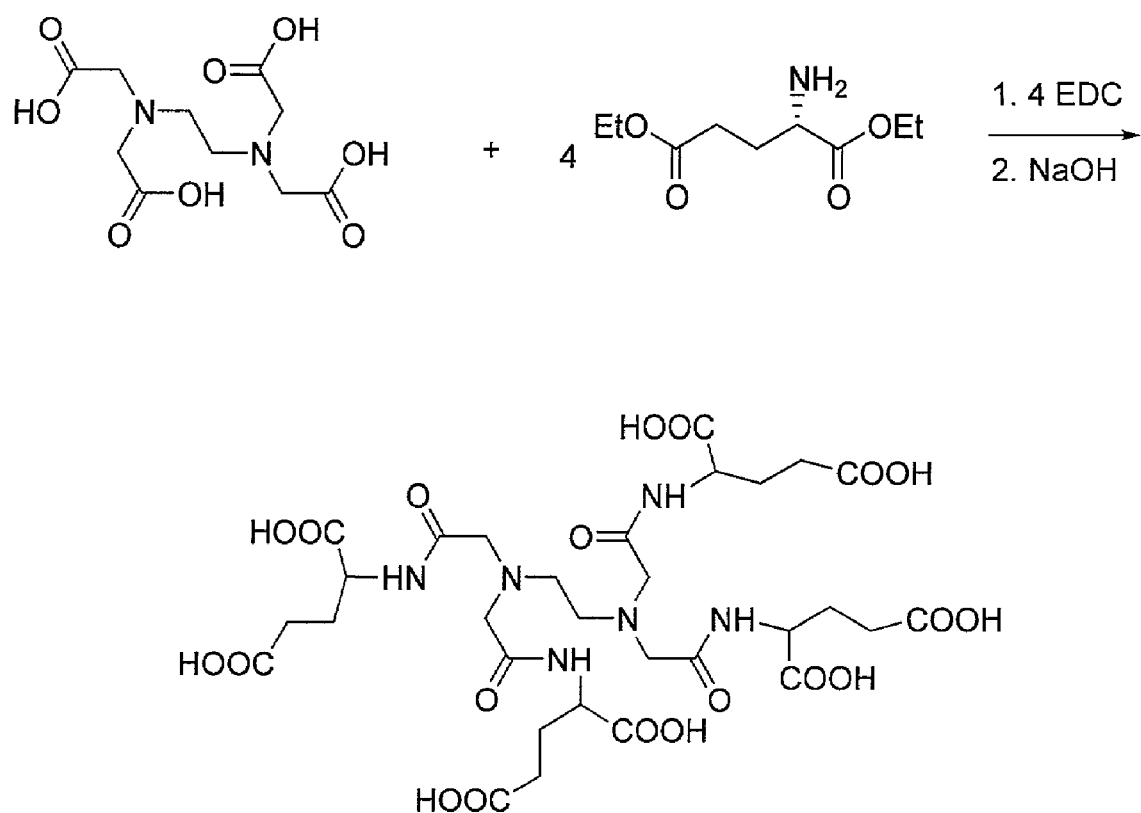
FIG. 4 shows a reaction scheme for producing [ETDA (Glu)$_4$].

(II) Carboxylic Acid Synthesis (Second Shell):

The purified coupling product [EDTA(Glu)$_4$] (100 mg) was dissolved in 5 ml THF, then 0.5 N aqueous sodium hydroxide (5 ml) was added. The resulting mixture was stirred at ambient temperature for 2 hours. The pH of the solution was then adjusted to about 8 by the slow addition of 1.0 N aqueous hydrogen chloride. The resulting solution was diluted with water (50 ml), and then subjected to lyophilization and dialysis (molecular weight cutoff 500) to furnish the free acid (with 8 carboxylic groups) as a white solid (Yield: not optimized). This reaction scheme is depicted in FIG. 4.

Block Synthesis

To a 100 ml round-bottomed flask, the following were successively added: N-tert-butoxycarbony-glutamic acid (746 mg), water (25 ml), and sodium hydroxide (240 mg). Glutamic acid diethyl ester (GDE) hydrochloride (1.44 g) and 1-ethyl-3-(3-dimethylaminopropyl) carboiimide (EDC) hydrochloride (1.15 g) were then added. A clear solution was formed. This solution was stirred at ambient temperature. Ten minutes later the solution became cloudy. At this point THF (25 ml) was added, and the solution turned clear again.

Figure 5:
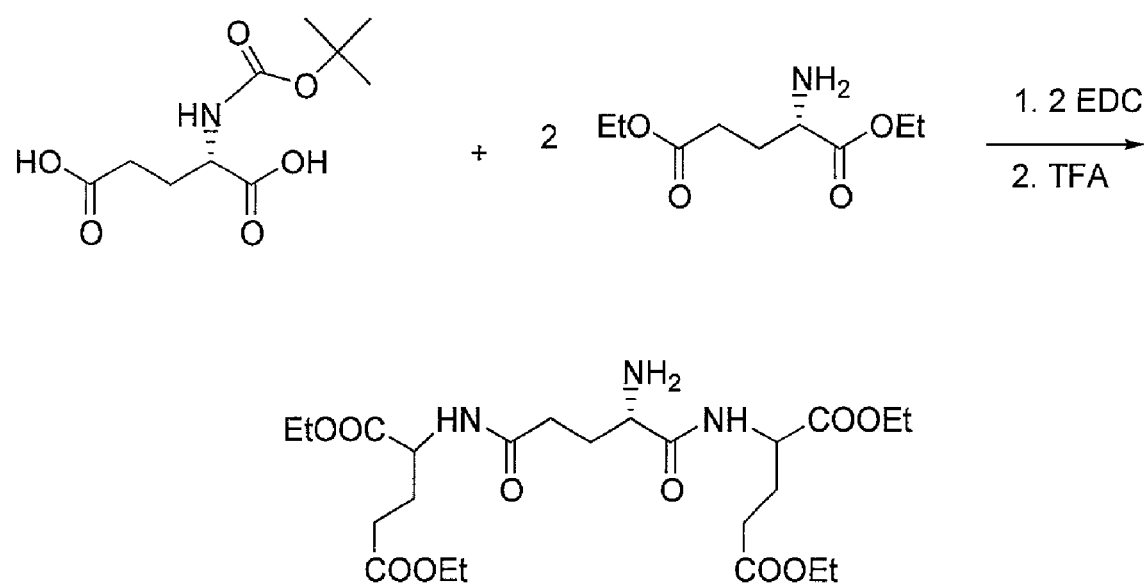
FIG. 5 shows a reaction scheme for producing [Glu(Glu)$_2$].

Stirring was continued for 5 hours. The reaction mixture was then partitioned between ethyl acetate (75 ml) and water (75 ml). The separated organic layer was washed with brine (50 ml), dried over anhydrous sodium sulfate (20 mg) and evaporated in a rotary evaporator under reduced pressure to give a colorless gel, which was purified over silica gel flash chromatography (1:1 ethyl acetate/hexane, then ethyl acetate) to furnish the product [Glu(Glu)$_2$] as a colorless solid (Yield: 86%). This reaction scheme is depicted in FIG. 5.

Figure 6:
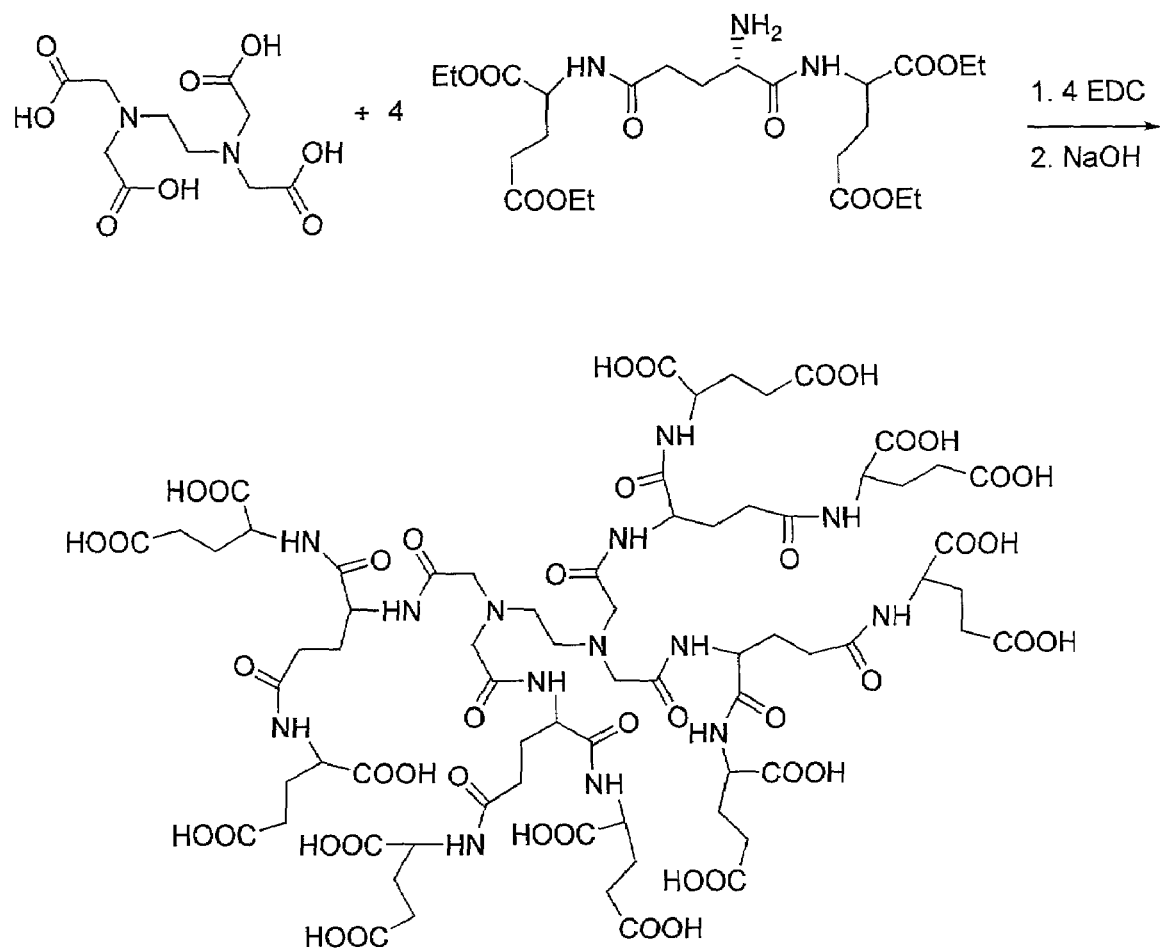
FIG. 6 shows a reaction scheme for producing a conjugate having 16 carboxylic acid groups.

Likewise, the [Glu(Glu)$_2$] product can be reacted with ETDA produce larger conjugate molecules, such as a conjugate having 16 carboxylic acid groups This embodiment is illustrated in FIG. 6.

Figure 7:
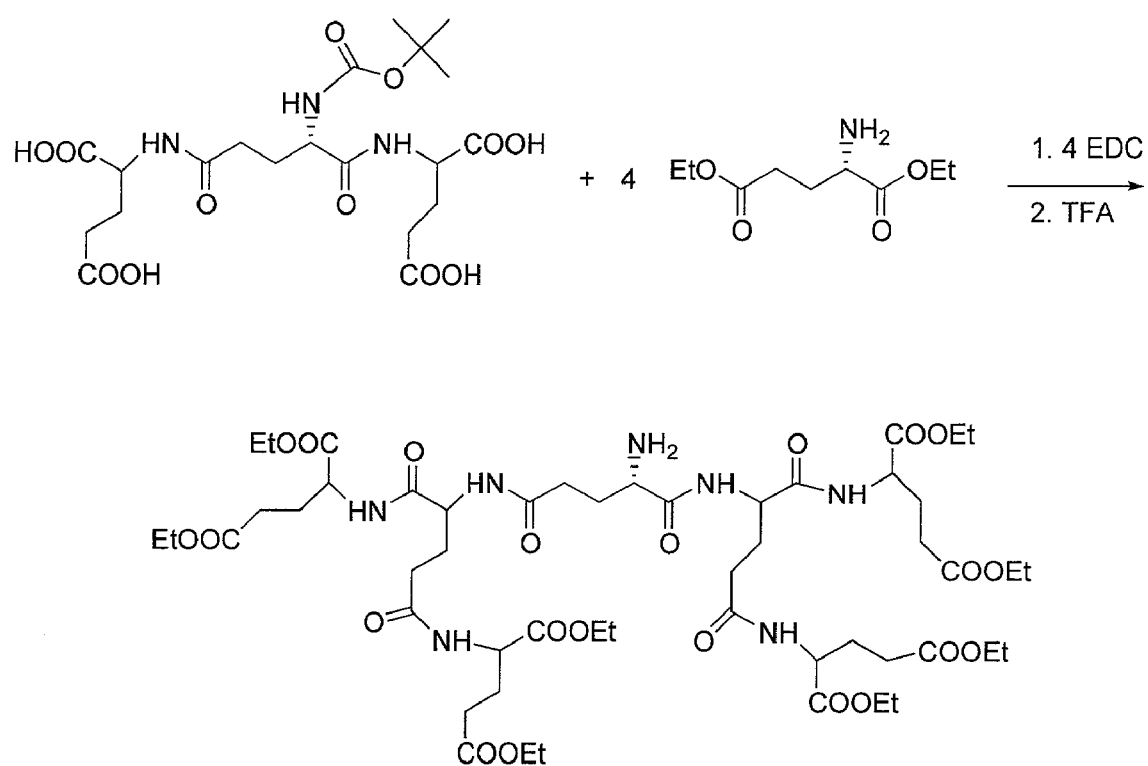
FIG. 7 shows a synthesis of a Glu[Glu(Glu)$_2$]$_2$ product.
Figure 8:
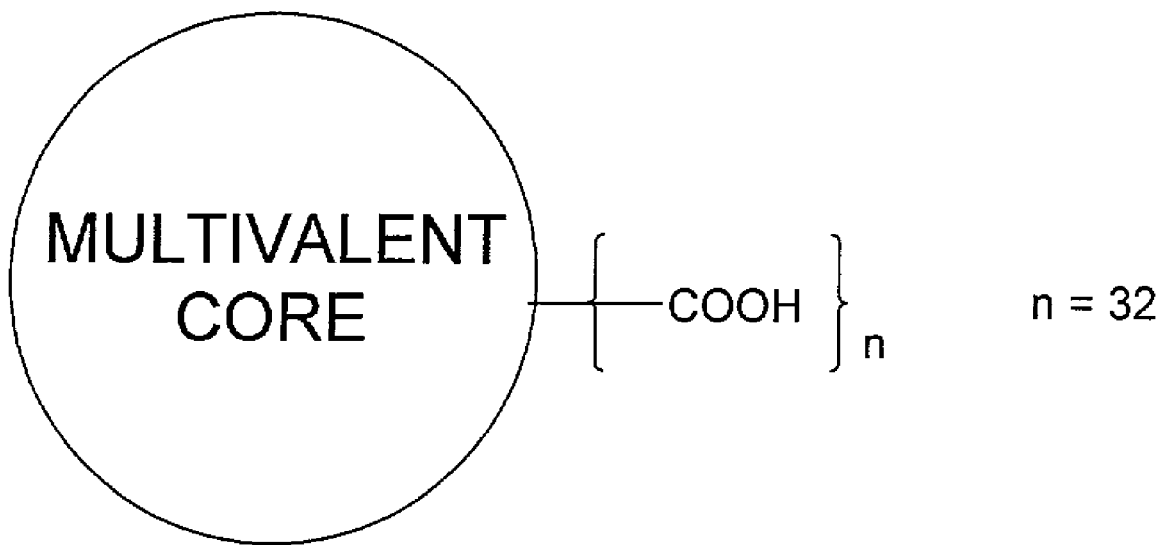
FIG. 8 shows conjugates of EDTA having 32 carboxylic acid groups.
Figure 9:
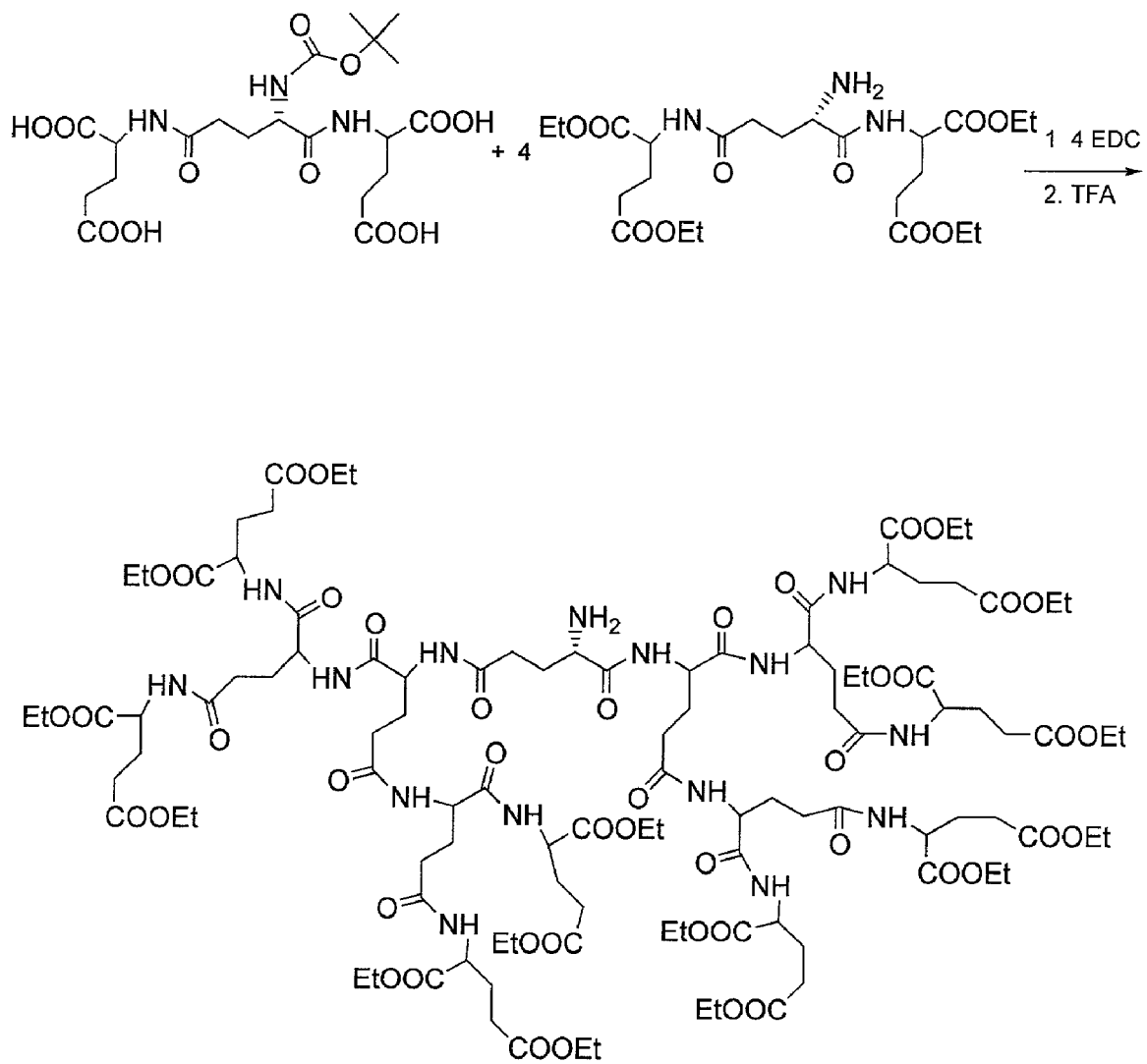
FIG. 9 shows a synthesis of a Glu[Glu[Glu(Glu)$_2$]$_2$]$_2$ product.
Figure 10:
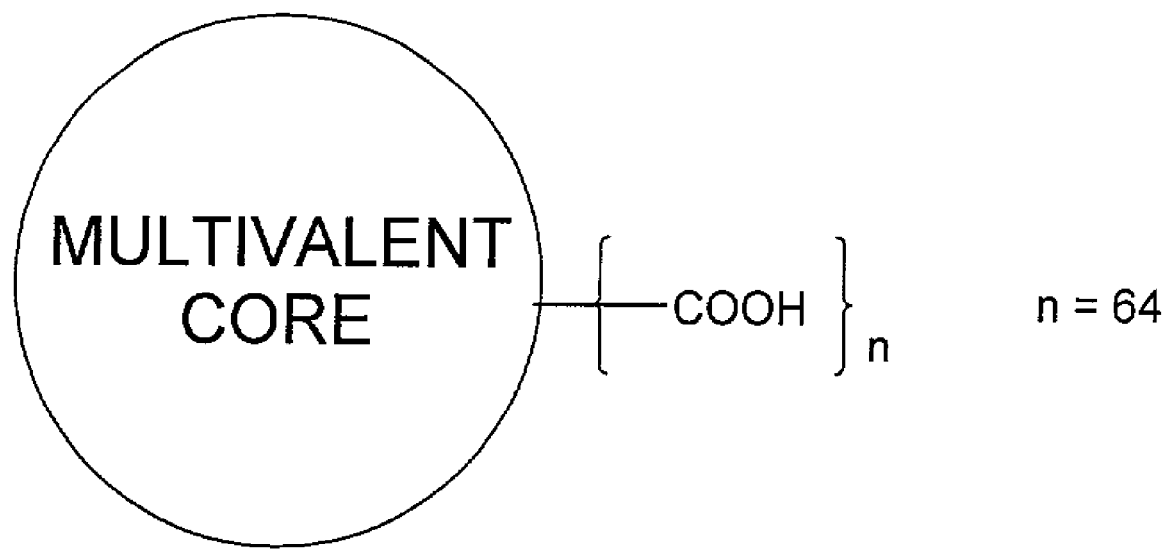
FIG. 10 shows an EDTA adduct having 64 carboxylic acid groups.

In a similar manner, an n-tert butoxy [Glu(Glu)$_2$] product can be reacted with EDC and GDE hydrochlorides (as described above) to produce [Glu[Glu(Glu)$_2$]$_2$] as shown in FIG. 7. Such molecules can be reacted with EDTA to produce conjugates of EDTA having 32 carboxylic acid groups as illustrated in FIG. 8. Alternatively, the n-tert butoxy [Glu(Glu)$_2$] product can be reacted with EDC and the [Glu(Glu)$_2$] product to produce a Glu[Glu[Glu(Glu)$_2$]$_2$]$_2$ as shown in FIG. 9, which can be conjugated to EDTA to produce conjugates of EDTA having 64 carboxylic acid groups. A molecular carrier having a multivalent core and 64 surface functional carboxylic acid groups is illustrated in FIG. 10.

Figure 11:
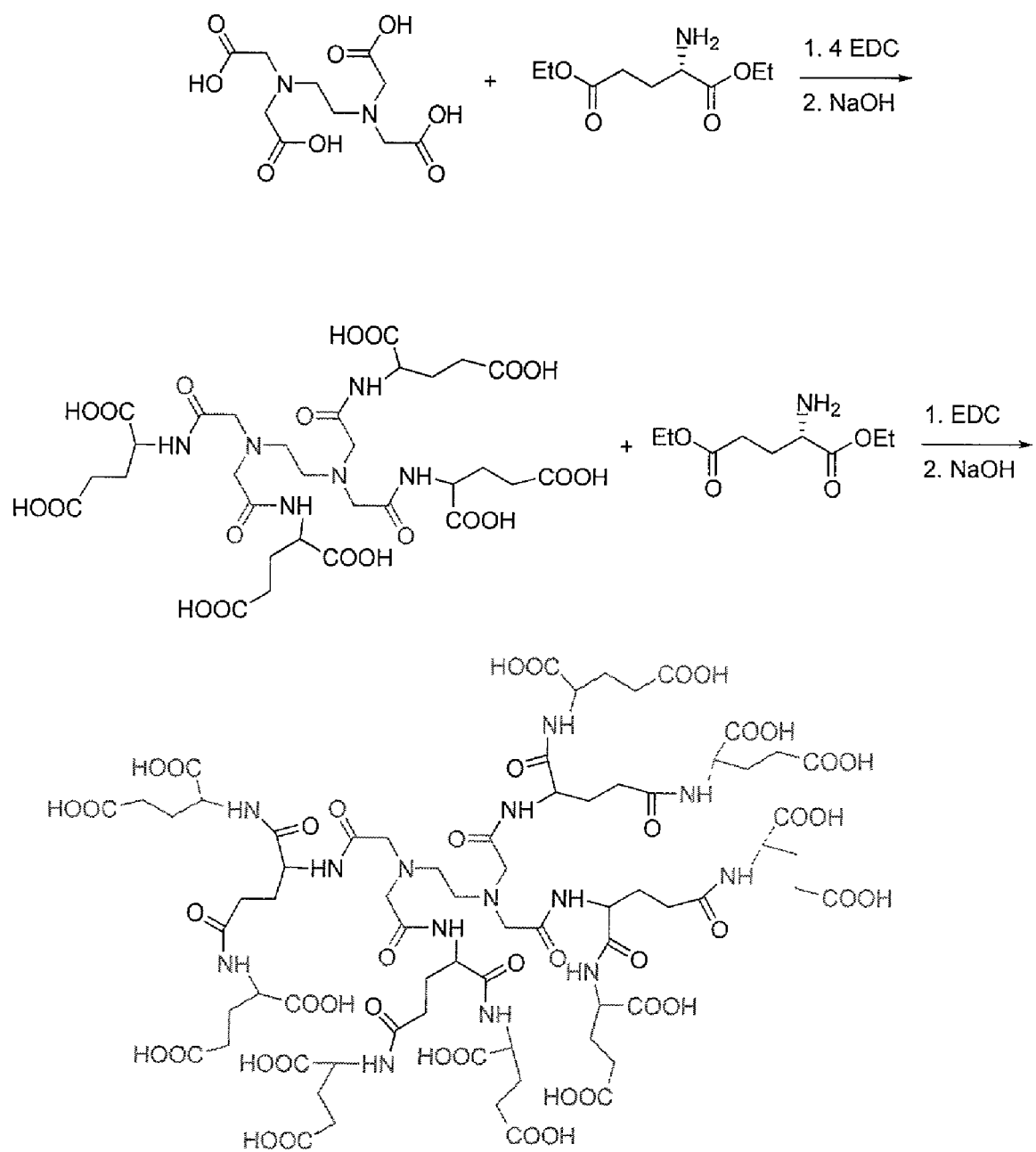
FIG. 11 shows a synthesis of an EDTA-[Glu(Glu)$_2$]$_4$ multi-functional carrier.
Figure 13:
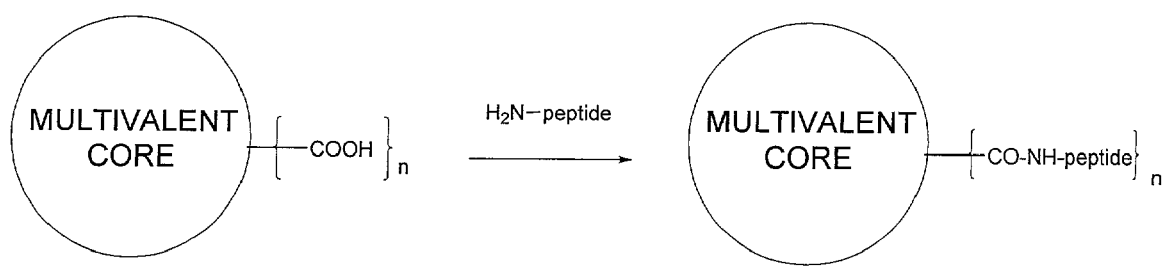
FIG. 13 shows a peptide covalently conjugated to a multi-functional carrier having an multivalent core.

FIG. 11 is an overview showing the synthesis of a conjugate of a peptide and an EDTA-[Glu(Glu)$_2$]$_4$ multifunctional carrier. Although a multi-functional carrier having 16 surface functional carboxylic acid groups is shown, the procedure can be continued to provide a higher generation multi-functional carrier having 32, 64, 128, etc. carboxylic acid groups. As shown in FIG. 13, a peptide can be covalently associated with the multi-functional carrier by reaction of an amino group on the peptide with the carboxylic acid surface functional group on the carrier.

EXAMPLE 2

Synthesis of Succinic Acid-Glutamic Acid Adducts

Succ-Glu 1st Shell:

(I) Ester synthesis: To a 50 ML round-bottomed flask was added 100 mg of succinic acid disodium salt (0.62 mmole) and water (10 ml). Glutamic acid diethyl ester hydrochloride (149 mg, 1.0 equivalent) was added in, followed by the addition of 1-ethyl-3-(3-dimethylaminopropyl)carbodiimide (EDC) hydrochloride (119 mg, 1.0 equivalent). A clear solution formed. This solution was stirred at ambient temperature. 30 minutes later, solution became cloudy, at this moment tetrahydrofuran (THF) (10 ml) was added in, solution turned clear again. Stirring was continued for 5 hours. The reaction mixture was then partitioned between ethyl acetate (20 ml) and water (20 ml). The separated organic layer was washed with 0.1N aqueous HCl solution (2×15 ml), and brine (15 ml), dried over anhydrous sodium sulfate (5 g) and evaporated in a rotary evaporator under reduced pressure to give the desired ester as a viscous oil. Yield: 95%. The molecular structure was confirmed by NMR and Mass Spectra.

(II) Carboxylic acid synthesis: The above ester was dissolved in 5 ml tetrahydrofuran (THF), then 0.25 N aqueous sodium hydroxide (10 ml) was added. The resulting homogeneous solution was stirred at ambient temperature for 2 hours. THF was evaporated in a rotary evaporator under reduced pressure. The remaining aqueous solution underwent lyophilization to furnish the desired acid (sodium salt) as a solid. Yield: 99%. Molecule structure was confirmed by NMR and Mass Spectra.

Peptide Preparation

Peptide T is an 8 amino acid peptide (mw=857) which is derived from the V2 region of HIV-1, inhibits replication of R5 and dual-tropic (R5/X4) HIV-1 strains in monocyte-derived macrophages (MDMs), microglia, and primary CD4 (+)T cells. Peptide T (D-Ala-Ser-Thr-Thr-Thr-Asn-Tyr-Thr-NH$_2$), a fragment corresponding to residues 185-192 of gp120, the coat protein of HIV, is endowed with several biological properties in vitro, notably inhibition of the binding of both isolated gp120 and HIV-1 to the CD4 receptor, and chemotactic activity. See, for example, Picone, et al., "Peptide T Revisited: Conformational Mimicry of Epitopes of Anti-HIV Proteins", J. Pept. Sci., 7, 4, 197-207 (2001). The peptide T was synthetically prepared using a commercial available peptide synthesizer and purified by reverse phase HPLC. The purified peptide was reconstituted in distilled water to a final concentration of 1 mg/ml and stored at −80° C.

Synthesis of 2nd, 3rd, and 4th Shell:

The same procedure as described above was used except that the glutamic acid diethyl ester hydrochloride and 1-ethyl-3-(3-dimethylaminopropyl) carbodiimide (EDC) hydrochloride were used in two fold excess, respectively.

Preparation of EDTA/or Succinic Acid-(Glu)$_n$-(Peptide T)$_{2n}$

EDTA—Glu 1$^{st}$ Shell and Peptide T:

| Acid: | 0.5 mg |
| Peptide T | 4.0 mg |
| EDC | 0.95 mg |

EDTA—Glu 2$^{nd}$ Shell and Peptide T:

| Acid: | 0.5 mg |
| Peptide T | 3.5 mg |
| EDC | 0.83 mg |

Succ-Glu 1st Shell and Peptide T:

| Acid: | 0.5 mg |
| Peptide T | 4.3 mg |
| EDC | 1.0 mg |

Succ-Glu 2nd Shell and Peptide T:

| Acid: | 0.5 mg |
| Peptide T | 3.6 mg |
| EDC | 0.86 mg |

Succ-Glu 3rd Shell and Peptide T:

| Acid: | 0.5 mg |
|---|---|
| Peptide T | 3.4 mg |
| EDC | 0.80 mg |

Synthesis of EDTA-(Glu)$_n$ or Succinic Acid-(Glu)$_n$ Conjugates with Peptide T 0.5 mg of each EDTA/or succinic acid-(Glu)$_n$ was dissolved in 1 ml of 0.1 M MES (2-N-morpholino ethanesulfonic acid), pH=4.75 at room temperature. After 1-ethyl-3-(3-dimethylaminopropyl)-carbodiimide hydrochloride (EDC) was added, the mixture was adjusted to pH=5.0 with 0.1 N HCl solution, and stirred at room temperature for 10 minutes. To this solution, peptide T (1 mg/ml, dissolved in deionized water) was added and the mixture placed on a rocker and rocked gently at room temperature for 4 hours. The resulting mixture was dialyzed against 4 liters deionized water 3 times with MWCO=3500 to remove free EDC. The distilled water was changed every 2 hours.

Figure 12:
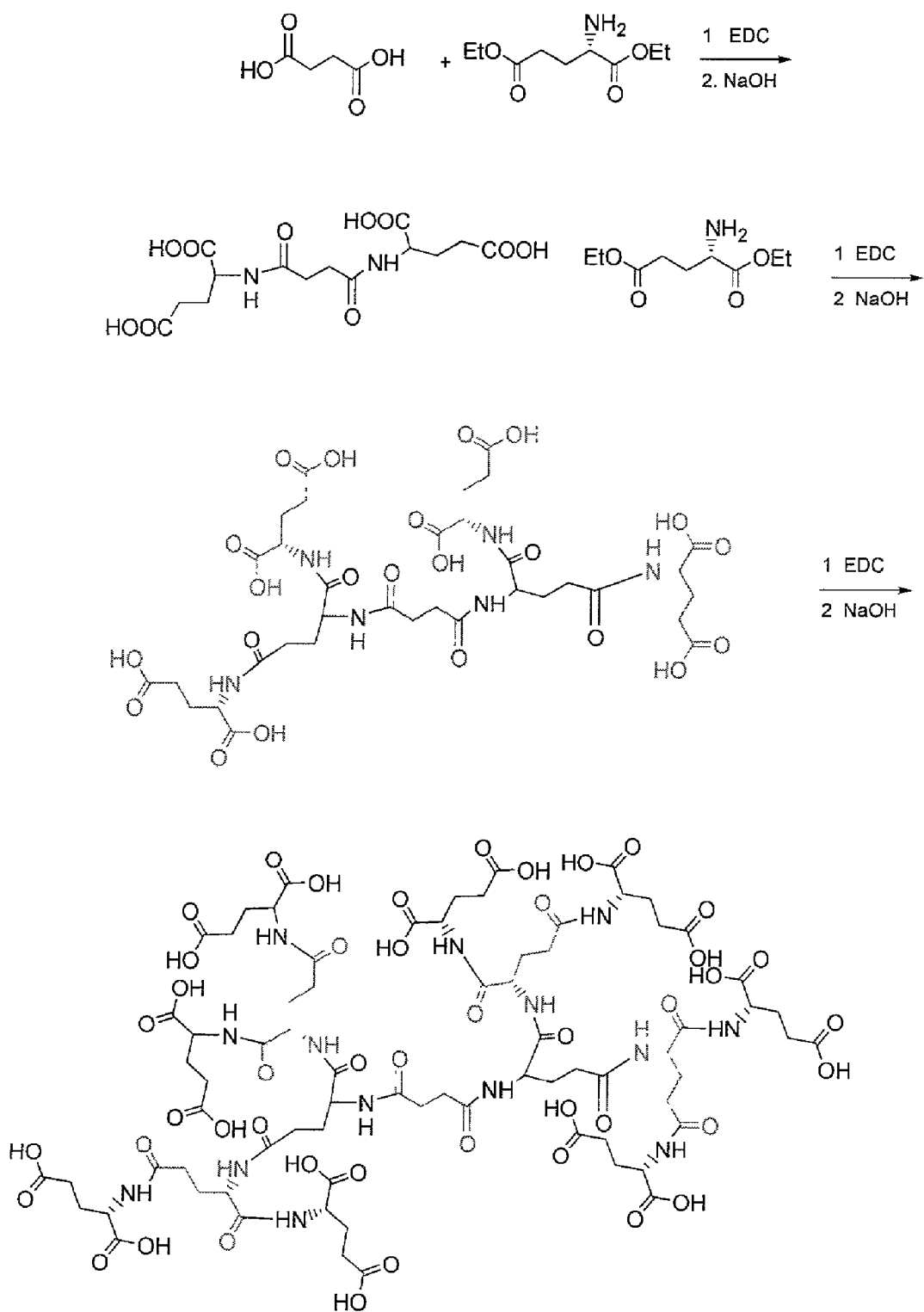
FIG. 12 shows a synthesis of a Succinic Acid-[Glu[Glu(Glu)$_2$]$_2$]$_2$ multi-functional carrier.

FIG. 12 is an overview showing the synthesis of a conjugate of a peptide and a Succinic Acid-[Glu[Glu (Glu)$_2$]$_2$]$_2$ multi-functional carrier. Although a multi-functional carrier having 16 surface functional carboxylic acid groups is shown, the procedure can be continued to provide a higher generation multi-functional carrier having 32, 64, 128, etc. carboxylic acid groups. As shown in FIG. 13, the peptide can be covalently associated with the multi-functional carrier by reaction of an amino group on the peptide with a carboxylic acid surface functional group on the carrier.

The resulting peptide T conjugate solution was further purified by C18-RP-HPLC.

| HPLC Method of Purification of Peptide-T Conjugates | | | | |
|---|---|---|---|---|
| Time | flow rate | A (%) | B (%) | curve |
| Initial | 5.0 | 0 | 100 | * |
| 12 | 5.0 | 20 | 80 | 6 |
| 12.5 | 5.0 | 0 | 100 | 11 |
| 16 | 0.1 | 0 | 100 | 11 |

Mobile phase A: 90% CH$_3$CN, 10% H$_2$O, 0.05% TFA

Mobile phase B: H$_2$O, 0.05% TFA

Phenomenex Jupitor 250×10 mm, C18, 5u, 300 A;

UV detector, detection wavelength: 225 nm,

Analysis of Conjugated Peptide T

HPLC fractions of succinic acid-(Glu)$_n$ conjugated to peptide T were analyzed by ELISA (i.e., enzyme linked immunosorbent assay). HPLC fractions of conjugated peptide T were diluted (1:10) in coating buffer [1.59 g sodium carbonate (Na2CO3), 2.93 g sodium bicarbonate (NaHCO3) Dissolve in 900 ml H2O, adjust pH to 9.6 with HCl and make up to 1 L]. Control net peptide T was dissolved in coating buffer with a concentration of 5 µg/ml. 100 µl of each of two peptide T preparations was added to each well of a 96-well microtiter plate (Nunc). The plate was covered with a plate sealer and incubated at 4° C. over night. Following 3 washes with PBS-Tween [phosphate buffer saline: 8.0 g sodium chloride (NaCl), 0.2 g monobasic potassium phosphate (KH$_2$PO$_4$), 1.15 g dibasic sodium phosphate (Na$_2$HPO$_4$), 0.2 g potassium chloride (KCl), Dissolve in 900 ml H$_2$O, adjust pH to 7.4 with NaOH or HCl and make up to 1 L, PBS+0.5 ml Tween 20 per liter]. 100 µl of diluted rabbit anti peptide T antiserum (1:250, in assay diluent, 0.1% BSA and 0.1% sodium azide (NaN$_3$) in PBS) was added to each well. The plate was sealed and incubated for 1 hour at room temperature. Following 5 washes, each well was added with 100 µl of diluted goat anti rabbit IgG alkaline phosphatase conjugate (KPL, 1:1000 dilution in assay diluent). The plate was sealed and incubated for 30 min. Following final washes, 100 µl of substrate solution [p-nitrophenyl phosphate from Sigma, 20 mg dissolved in 10 ml substrate buffer, 0.844 g sodium bicarbonate (NaHCO$_3$), 1.255 g sodium carbonate (Na$_2$CO$_3$), 0.203 g magnesium chloride (MgCl$_2$.6H$_2$O), dissolve in 1000 ml H$_2$O] was added to each well. Optical density (OD) was then read at 405 nm.

Figure 14:
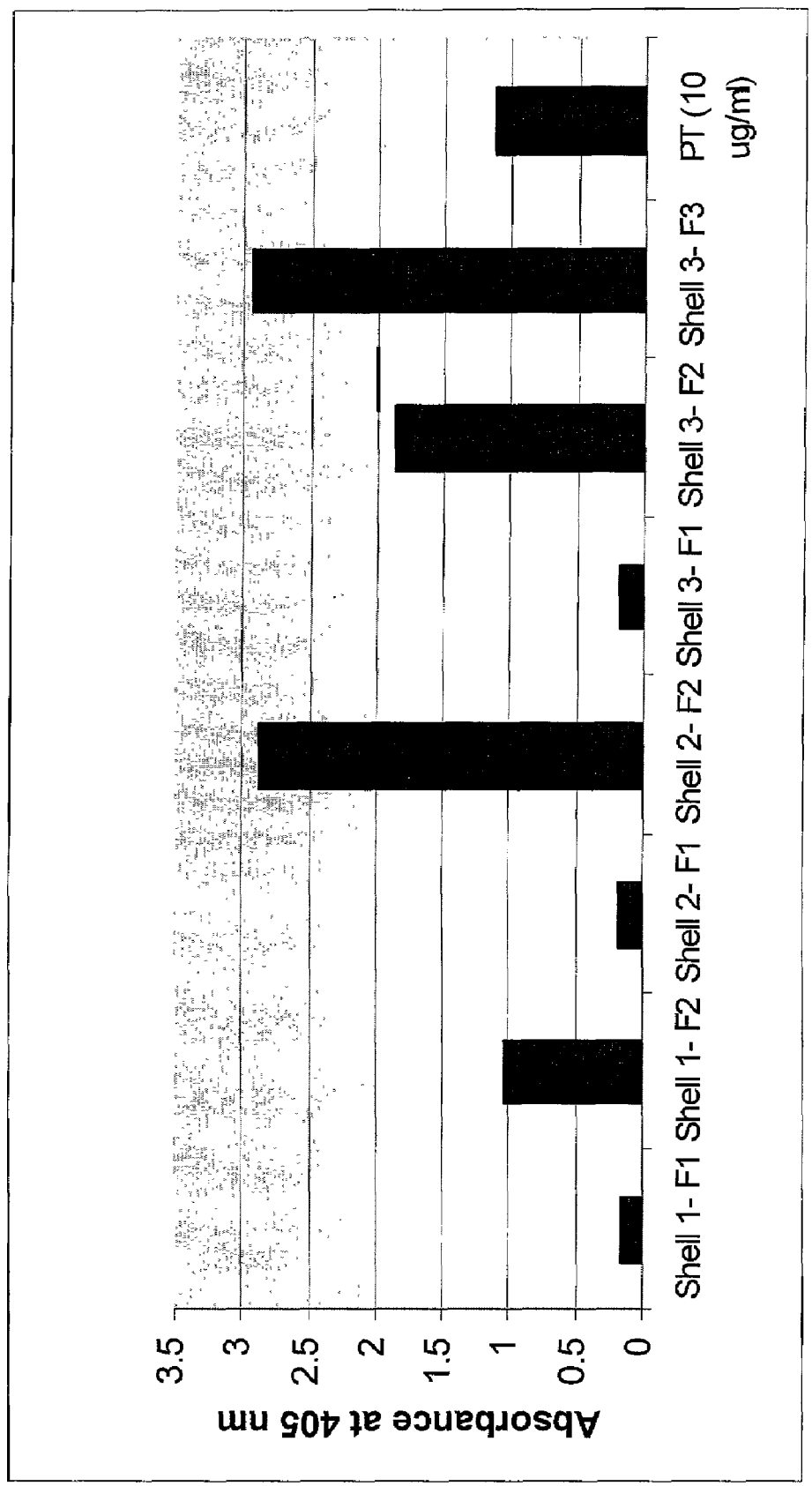
FIG. 14 is a bar chart showing optical density at 405 nm for HPLC fractions of succinic acid-(Glu)$_n$ adducts conjugated to peptide T analyzed by an ELISA.

The results are shown in FIG. 14 which is a bar chart showing optical density at 405 nm of different HPLC fractions (F1, F2 and F3) for various Succinic Acid-(Glu)$_n$ adducts conjugated to Peptide T and for a control. In FIG. 14, Shell 1 refers to Succinic Acid-(Glu)$_2$-(Peptide T)$_4$ conjugates; Shell 2 refers to Succinic Acid-(Glu)$_2$-(Glu)$_4$-(Peptide T)$_8$ conjugates; Shell 3 refers to Succinic Acid-(Glu)$_2$-(Glu)$_4$-(Glu)$_8$-(Peptide T)$_{16}$ conjugates; F refers to the HPLC fraction with F1 being the fraction with the lowest retention time and F3 being the fraction with the highest retention time; and PT refers to Free peptide-T. The results shown in FIG. 14 indicate that there are different populations of peptide T conjugated to each adduct. For the Shell 2 and Shell 3 adducts, as the amount of peptide T coupled to the molecular carrier increases (which is shown by its immunoreactivity), the retention time of HPLC increases (i.e., from Fraction #1 to Fraction #3). That is, for the Shell 3 adduct, Fraction 3, which has the highest retention time, also has the highest immunoreactivity. Similarly, for the Shell 2 adduct, Fraction 2, which has the highest retention time, also has the highest immunoreactivity. Measuring molecular weight of each fraction using Mass Spectrum analysis should reveal the actual coupling efficiency of the peptide to the molecular carrier.

Immunization Procedures for Mouse Polyclonal Antibodies to the Succinic Acid-(Glu)n-Peptide T Conjugate Balb/c mice were immunized intraperitoneally with succinic acid-(glu)n-Peptide T at 0.5 mg per immunization and per animal. The antigen complex was administered with complete Freund's adjuvant (first injection) and with incomplete Freund's adjuvant for booster injections. Mice were immunized 3 times at day 0, day 8 and day 21. Mice were bled via tail vein and 15 µl of blood collected by a capillary tube was transferred into 135 µl PBS in a 12×75 tissue culture tube. Diluted mouse sera were collected after centrifugation for 10 min.

ELISA Procedures for Mouse Polyclonal Antibodies to the Succinic Acid-(Glu)n-Peptide T Conjugate A polystyrene 96-well plate (Nunc) was coated with free peptide T at 10 µg/ml in coating (pH 9.6) overnight at 4° C.

The plate was washed 3 times with wash buffer. Afterwards, 100 μl of diluted (1:100 in assay diluent) mouse antiserum from each mouse was then added to each well (each serum sample was assayed in duplicate) and incubated for 2 hours at room temperature. The plates were then washed 5 times with wash buffer. Goat anti-mouse IgG conjugated to alkaline phosphate (KPL) was diluted 1:1000 in PBS with 1% bovine serum albumin, added to the wells, and incubated for 30 min at room temperature followed by six washes with wash buffer. Substrate solution (p-Nitrophenyl phosphate, 2 mg/ml in substrate buffer) was then added. Absorbance was then measured using a microplate reader at 405 nm. The results are shown in FIG. 15 wherein each bar represents an average OD value of one mouse antiserum.

Figure 15:
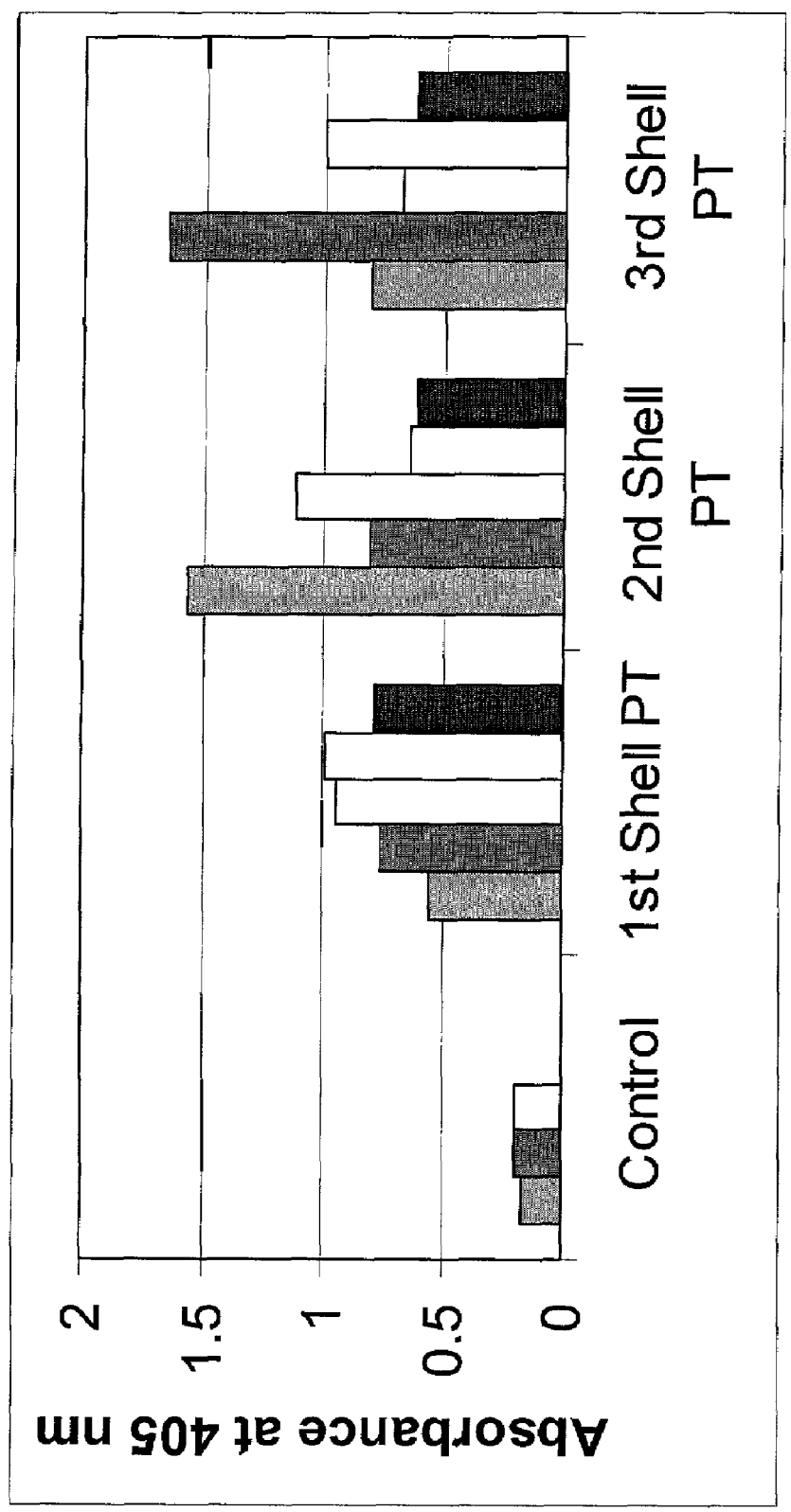
FIG. 15 is a bar chart showing optical density at 405 nm for mouse polyclonal antibodies to succinic acid-(Glu)$_n$ adducts conjugated to peptide T analyzed by an ELISA.

The ELISA results shown in FIG. 15 demonstrate that peptide T, when conjugated to different succinic acid-(glu)$_n$ shells, induced a significant immune response in mice. Further, some mice show greater immune response to both Shell 2-Peptide T and Shell 3-Peptide stimulations than other animals.

All publications and patent applications mentioned in the specification are herein incorporated by reference to the same extent as if each individual publication or patent application had been specifically and individually indicated to be incorporated by reference. The discussion of the background to the invention herein is included to explain the context of the invention. Such explanation is not an admission that any of the material referred to was published, known, or part of the prior art or common general knowledge anywhere in the world as of the priority date of any of the aspects listed above.

While the invention has been described in connection with specific embodiments thereof, it will be understood that it is capable of further modifications and that this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A molecular carrier comprising a central multivalent core and a plurality of adduct molecules bonded thereto, wherein the molecular carrier is represented by the formula:

or by the formula:

wherein n is an integer of 2 or greater, m is 0 or a positive integer and p is a positive integer and wherein "Adduct" represents adduct moieties which can be the same or different from one another and wherein the adduct moieties comprise the residue of an amino acid.

2. The molecular carrier of claim 1 wherein the molecular carrier is represented by the formula:

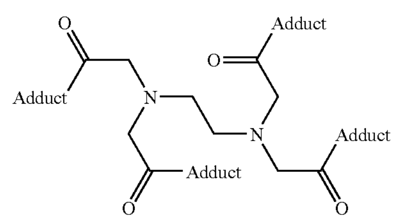

wherein the adduct moieties comprise the residue of an amino acid.

* * * * *